United States Patent

Conrad et al.

[11] Patent Number: 6,028,200
[45] Date of Patent: Feb. 22, 2000

[54] PROCESS FOR PREPARING 2-CHLORO-BENZIMIDAZOLE DERIVATIVES

[75] Inventors: Michael Conrad, Wuppertal; Lutz Assmann, St Peter-Ording; Heinz-Jürgen Wroblowsky, Langenfeld; Carl Casser, Köln; Dietmar Bielefeldt, Ratingen, all of Germany

[73] Assignee: Bayer Aktiengesellschaft, Leverkusen, Germany

[21] Appl. No.: 09/307,591

[22] Filed: May 7, 1999

Related U.S. Application Data

[62] Division of application No. 09/118,954, Jul. 17, 1998.

[30]     Foreign Application Priority Data

Jul. 22, 1997 [DE] Germany ............................ 197 31 799
Oct. 16, 1997 [DE] Germany ............................ 197 45 692

[51] Int. Cl.⁷ ............................................. C07D 235/02
[52] U.S. Cl. ............................................. 548/302.1
[58] Field of Search ................................... 548/302.1

[56]     References Cited

U.S. PATENT DOCUMENTS

| | | | |
|---|---|---|---|
| 4,435,406 | 3/1984 | Krasso et al. ............................ | 424/263 |
| 4,560,693 | 12/1985 | Rainer ..................................... | 514/338 |
| 4,686,230 | 8/1987 | Rainer et al. ............................ | 514/338 |
| 4,758,579 | 7/1988 | Kohl et al. ............................... | 514/338 |
| 4,766,133 | 8/1988 | Fischli et al. ........................... | 514/338 |
| 5,587,389 | 12/1996 | Kohl et al. ............................... | 514/338 |

FOREIGN PATENT DOCUMENTS

| | | |
|---|---|---|
| 3605977 | 8/1987 | Germany . |
| 196 09 060 | 2/1997 | Germany . |
| 86/02645 | 5/1986 | WIPO . |
| 87/01114 | 2/1987 | WIPO . |
| 89/05299 | 6/1989 | WIPO . |
| 89/11479 | 11/1989 | WIPO . |
| 97/06171 | 2/1997 | WIPO . |

OTHER PUBLICATIONS

J. Chem. Soc. (month unavailable) 1963) 2930–37.
Patent Abstract of Japan, vol. 12, No. 433 (C–543), Nov. 1998 & JP 63 159383 A (Taisho Pharmaceut Co Ltd) Jul. 2, 1998.

*Primary Examiner*—Laura L. Stockton
*Attorney, Agent, or Firm*—Joseph C. Gil; Carol Marmo

[57]     ABSTRACT

A novel process for the preparation of 2-chloro-benzimidazole derivatives of the formula

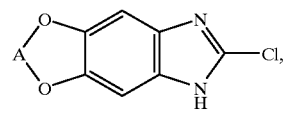

(I)

in which

A represents optionally halogenated alkylene having 1 or 2 carbon atoms, which process comprises reacting 1,3-dihydro-benzimidazol(ethi)ones of the formula

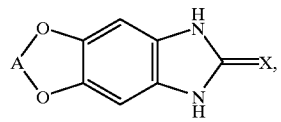

(II)

in which

X represents oxygen or sulphur, with phosphorus oxychloride.

Novel 1,3-dihydro-benzimidazol(ethi)ones of the formula (II) and processes for their preparation.

2 Claims, No Drawings

PROCESS FOR PREPARING 2-CHLORO-BENZIMIDAZOLE DERIVATIVES

This application is a divisional of application Ser. No. 09/118,954, filed Jul. 17, 1998.

TECHNICAL FIELD OF THE INVENTION

The present invention relates to a novel process for preparing known 2-chloro-benzimidazole derivatives which can be used as intermediates for synthesizing active compounds having microbicidal properties. Furthermore, the invention relates to novel 1,3-dihydro-benzimidazol(ethi)ones and to a process for their preparation.

BACKGROUND OF THE INVENTION

It is already known that benzimidazole derivatives chlorinated in the 2 position can be prepared by reacting the corresponding 2-bromo-imidazoles with hydrogen chloride (cf. WO-A 97-06171). Thus, for example by treating 2-bromo-6,6-difluoro-[1 with 3]dioxolo-[4,5-f] benzimidazole with hydrogen chloride in the presence of dimethylformarnide, 2-chloro-6,6-difluoro-[1,3] dioxolo-[4,5-f]-benzimidazole is obtained. However, this process has the disadvantage that the desired products are obtained in relatively low yields.

Furthermore, it is already known that 2-chloro-benzimidazole can be prepared by reacting 1,3-dihydro-benzimidazol-2-one with phosphorus oxychloride in the presence of hydrogen chloride (cf. J. Chem. Soc. 1963, 2930). However, corresponding chlorinations of 1,3-dihydro-benzirnidazol-2-ones which contain a further fused-on heterocyclic ring on the benzene such as 1,3-dihydro-benzimidazol(ethi)ones of the present invention, ring have hitherto not been described.

SUMMARY OF THE INVENTION

It has now been found that 2-chloro-benzimidazole derivatives of the formula

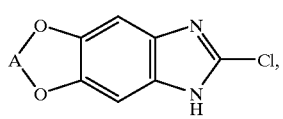

(I)

in which

A represents optionally halogenated alkylene having 1 or 2 carbon atoms, can be obtained by reacting 1,3-dihydro-benzirnidazol(ethi)ones of the formula

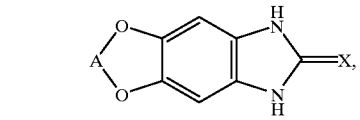

(II)

in which

A is as defined above and

X represents oxygen or sulphur, with phosphorus oxychloride, if appropriate in the presence of hydrogen chloride or of phosphorus pentachloride, and if appropriate in the presence of a diluent at temperatures between 50° C. and 150° C.

It is very surprising that 2-chloro-benzimidazole derivatives of the formula (I) can be prepared by the process according to the invention in substantially higher amounts than by the prior art method. It is also unexpected that specifically phosphorus oxychloride is particularly suitable for chlorination of 1,3-dihydro-benzirnidazol(ethi)ones of the formula (II).

DETAILED DESCRIPTION OF THE INVENTION

The process according to the invention has a number of advantages. Thus, as already mentioned, the process facilitates the synthesis of 2-chloro-benzimidazole derivatives of the formula (I) in very high yields. It is also advantageous that the reaction components which are required can be prepared in a simple manner and are available even in relatively large amounts. Finally, it is a further advantage that carrying out the reaction and isolating the reaction products does not cause any problems.

Using 6,6-difluoro-[1,3]dioxolo-[4,5-f]-1,3-dihydro-benzimidazol-2-one as starting material and phosphorus oxychloride in the presence of gaseous hydrogen chloride as chlorinating agent, the course of the process according to the invention can be illustrated by the equation below.

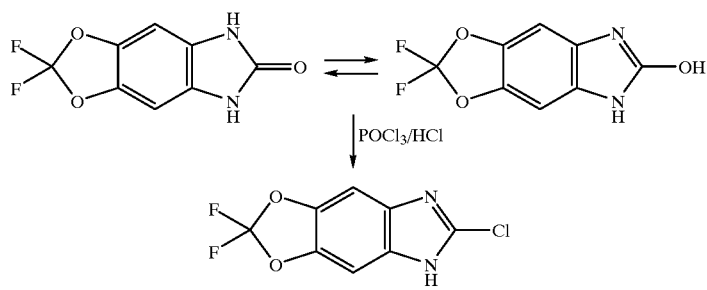

The formula (II) provides a general definition of the 1,3-dihydro-benzimidazol(ethi)ones required as starting materials for carrying out the process according to the invention. Preference is given to compounds of the formula (II), in which represents ethylene which is optionally mono- to tetrasubstituted by fluorine and/or chlorine and X represents oxygen or sulphur.

Particular preference is given to 1,3-dihydro-benzimidazol(ethi)ones of the formula (II) in which A represents the groups —CH$_2$—, —CF$_2$—, —CCl$_2$—, —CF$_2$—CF$_2$—, —CHF—CF$_2$, —CHF—CHF—, —CF$_2$—CFCl— or —CFCl—CFCl— and X represents oxygen or sulphur.

The 1,3-dihydro-benzimidazol(ethi)ones of the formula (II) have hitherto not been known. They can be prepared by reacting phenylenediamines of the formula

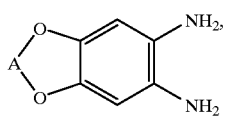

(III)

in which

A is as defined above, either
  a) with phosgene of the formula

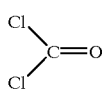

(IV)

in the presence of a diluent at temperatures between 10° C. and 120° C., or
  b) with 1,1-carbonyl-diimidazole of the formula

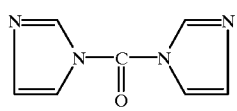

(V)

in the presence of a diluent at temperatures between 10° C. and 800° C., or
  c) with urea of the formula

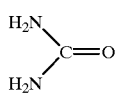

(VI)

if appropriate in the presence of a diluent at temperatures between 130° C. and 200° C., or
  d) with potassium O-ethyl-xanthate of the formula

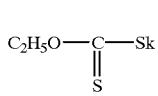

(VII)

in the presence of a diluent at temperatures between 20° C. and 100° C.

Using 5,6-diamino-2,2-difluoro-benzodioxole and phosgene as starting materials, the course of the above process can be illustrated by the equation below.

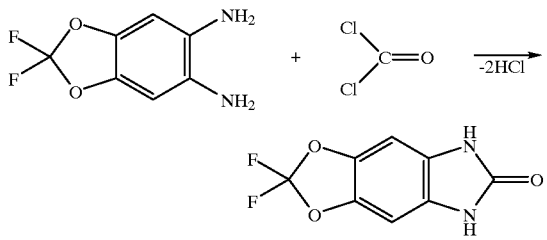

The formula (III) provides a general definition of the phenylenediamines required as starting materials for carrying out the above process for preparing 1,3-dihydro-benzimidazol(ethi)ones. Preference is given to compounds of the formula (m) in which A has those meanings which have already been mentioned in connection with the description of the 1,3-dihydro-benzimidazol(ethi)ones of the formula (II) as being preferred for A.

The phenylenediamines of the formula (III) are known or can be prepared by known processes (cf. DE-A 36 05 977 and WO 97-06171).

The compounds of the formulae (IV) to (VII) required as reaction components for carrying out the above process for preparing 1,3-dihydro-benzimidazol(ethi)ones of the formula (II) according to variants (a) to (d) are known.

Suitable diluents for carrying out the variant (a) of the above process are inert inorganic and organic solvents. Preference is given to using water, aqueous hydrochloric acid and halogenated aliphatic or aromatic hydrocarbons, such as methylene chloride, chloroform, carbon tetrachloride or chlorobenzene.

When carrying out the variant (a) of the above process, the reaction temperatures can be varied within a relatively wide range. In general, variant (a) is carried out at temperatures between 10° C. and 120° C., preferably between 20° C. and 110° C.

The variant (a) of the above process is generally carried out under atmospheric pressure. However, it is also possible to operate under elevated pressure.

When carrying out the variant (a) of the above process, preferably 1 to 5 mol of phosgene of the formula (IV) are employed per mole of phenylenediamine of the formula (III). Work-up of the product to recover the resultant 1,3-dihydro-benzimidazol(ethi)ones is carried out by customary methods. In general, after the phosgenation has ended, the resulting solid is filtered off, washed and dried.

Suitable diluents for carrying out the variant (b) of the above process are customary inert organic solvents. Preference is given to using ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole.

When carrying out the variant (b) of the above process, the reaction temperatures can bevaried within a certain range. In general, variant (b) is carried out at temperatures between 10° C. and 80° C., preferably between 20° C. and 70° C.

The variant (b) of the above process is generally carried out under atmospheric pressure. However, it is also possible to operate under elevated pressure.

When carrying out the variant (b) of the above process, generally an equivalent amount or else an excess, preferably 1.1 to 1.5 mol, of 1,1-carbonyl-diimidazole of the formula (V) is employed per mole of phenylenediamine of the formula (III). Work-up is carried out by customary methods. In general, the reaction mixture is poured onto dilute aqueous mineral acid, extracted repeatedly with an organic solvent which is sparingly miscible with water, and the combined organic phases are washed, dried and concentrated under reduced pressure. The product that remains can be freed from any impurities that may still be present using customary methods, such as recrystallization or chromatography.

The variant (c) of the above process is preferably carried out in the melt in the absence of any additional diluents. Here, the reaction temperatures can be varied within a certain range. In general, variant (c) is carried out at temperatures between 130° C. and 200° C., preferably between 140° C. and 190° C.

However, it is also possible to carry out the variant (c) of the above process in the presence of diluents, such as, for example, dimethylformamide or diethylene glycol.

The variant (c) of the above process is generally carried out under atmospheric pressure. However, it is also possible to operate under elevated or reduced pressure.

When carrying out the variant (c) of the above process, generally an equivalent amount or else an excess, preferably 2 to 4 mol, of urea of the formula (VI) is employed per mole of phenylenediamine of the formula (III). Work-up is carried out by customary methods. In general, the reaction mixture is admixed with dilute aqueous alkali metal hydroxide solution, the resulting mixture is filtered, the filtrate is acidified and the resulting precipitate is filtered off, washed and dried.

Suitable diluents for carrying out the variant (d) of the above process are customary inert organic solvents. Preference is given to using alcohols, such as methanol, ethanol, n-propanol or isopropanol.

When carrying out the variant (d) of the above process, the reaction temperatures can likewise be varied over a relatively wide range. In general, variant (d) is carried out at temperatures between 20° C. and 100° C., preferably between 30° C. and 90° C.

The variant (d) of the above process is also generally carried out under atmospheric pressure. However, it is also possible to operate under elevated or reduced pressure.

When carrying out the variant (d) of the above process, generally an equivalent amount or else an excess, preferably 1.1 to 1.5 mol, of potassium O-ethyl-xanthate of the formula (VII) is employed per mole of phenylenediamine of the formula (III). Work-up is again carried out by customary methods. In general, the reaction mixture, if appropriate after prior treatment with activated carbon, is filtered, the filtrate is admixed with water and acidified, and the resulting precipitate is filtered off with suction, washed and dried.

A suitable reaction component for carrying out the process according to the invention is phosphorus oxychloride, if appropriate in the presence of hydrogen chloride or of phosphorus pentachloride.

Suitable diluents for carrying out the process according to the invention are phosphorus oxychloride and halogenated aliphatic or aromatic hydrocarbons, such as dichloromethane, chloroform, carbon tetrachloride, dichloroethane, trichloroethane, chlorobenzene or dichlorobenzene. Preference is given to using phosphorus oxychloride both as reaction component and as diluent.

When carrying out the process according to the invention, the reaction temperatures can be varied within a relatively wide range. In general, the process is carried out at temperatures between 50° C. and 150° C., preferably between 70° C. and 130° C.

The process according to the invention is generally carried out under atmospheric pressure. However, it is also possible to operate under elevated pressure. In a preferred variant of the process according to the invention, the process is carried out in a sealed pressure vessel under the resulting autogenous pressure.

When carrying out the process according to the invention, generally such a high excess of phosphorus oxychloride is employed per mole of 1,3-dihydro-benzimidazol(ethi)one of the formula (II) that the former acts both as reaction component and as diluent. Furthermore, if appropriate, gaseous hydrogen chloride is introduced into the reaction mixture, or phosphorus pentoxide is added. Work-up is carried out by customary methods. In general, the reaction mixture is concentrated under reduced pressure, the residue is admixed with ice or water and the resulting precipitate is filtered off with suction, washed and dried. The acidic filtrate is neutralized by addition of aqueous base and the resulting precipitate is also filtered off with suction, washed and dried.

The 2-chloro-benzimidazole derivatives of the formula (I) preparable by the process according to the invention are useful intermediates for the synthesis of active compounds having microbicidal, preferably fungicidal, properties (cf. WO-A 97-06 171). Thus, fungicidally active chlorobenzimidazoles of the formula

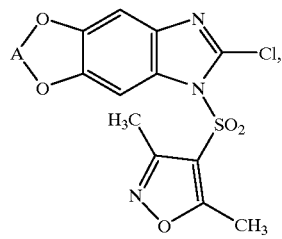

(VIII)

in which

A is as defined above, can be prepared by reacting 2-chlorobenzimidazole derivatives of the formula

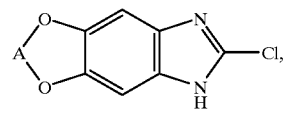

(I)

in which

A is as defined above, with 3,5-dimethyl-isoxazole4-sulphonyl chloride of the formula

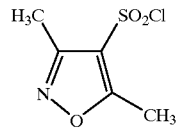

(IX)

in the presence of an acid binder, such as sodium hydride or potassium carbonate, and in the presence of a diluent, such as tetrahydrofuran or acetonitrile.

The implementation of the process according to the invention is illustrated by the following examples.

PREPARATION EXAMPLES

Example 1

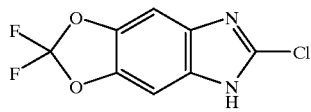
(I-1)

A mixture of 10 g (44 mmol) of 6,6-difluoro-[1,3]dioxolo-[4,5-f]-1,3-dihydro-benzimidazol-2-one and 100 ml of freshly distilled phosphorus oxychloride is heated under reflux for 15 minutes. The mixture is then heated for a further 6 hours under reflux, during which time gaseous hydrogen chloride is introduced at a rate of approximately 8 bubbles per second. The reaction mixture is subsequently concentrated under reduced pressure to a point where it can still be stirred easily. The residue is admixed with 100 g of ice and stirred at 5° C. for 16 hours. The residue that is obtained is filtered off with suction, washed with water and dried over phosphorus pentoxide. This gives 3.5 g of a product which consists essentially of 2-chloro-6,6-difluoro-[1,3]dioxolo[4,5-f]benzimidazole.

The acidic filtrate is neutralized with cooling with concentrated ammonia solution. The resulting mixture is stirred at 5° C. for 40 minutes. The solid that is obtained is filtered off with suction, washed with water and dried over phosphorus pentoxide. This gives 9 g of a product which consists to 80% of 2-chloro-6,6-difluoro[1,3]dioxolo[4,5-f]-benzimidazole.

This corresponds to a total yield of 85% of theory of 2-chloro-6,6-difluoro[1,3]dioxolo[4,5-f]-benzimidazole.

Example 2

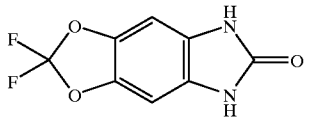
(II-1)

At room temperature, first 5.0 kg of phosgene at a dosage rate of 1.7 kg/h and then a further 3.5 kg of phosgene at a dosage rate of 0.6 kg/h are introduced with stirring into a mixture of 9.4 kg (46.2 mol) of 5,6-diamino-2,2-difluoro-benzodioxole and 47 kg of water, the temperature of the reaction mixture rising to 45° C. The reaction mixture is stirred at this temperature for 13 hours and a further 0.34 kg of phosgene are then added. The reaction mixture is allowed to cool to room temperature, the reaction vessel is flushed with nitrogen and 15.8 kg of a 45% strength by weight aqueous sodium hydroxide solution are added to neutralize the reaction mixture. The resulting precipitate is filtered off with suction, washed a little at a time with a total of 50 kg of water and dried under reduced pressure at a temperature of 60° C. In this manner, 9.85 kg (91.8% of theory) of 6,6-difluoro-[1,3]dioxolo-[4,5-f]-1,3-dihydro-benzimidazol-2-one are obtained in the form of a solid substance having a melting point of more than 220° C.

$^1$H NMR spectrum (DMSO, TMS): δ=7.05 ppm (s, 2H, CH); δ=10.8 ppm (s, 2H, NH).

Example 3

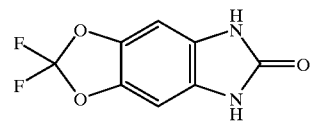
(II-1)

At 30 to 40° C., 150 g of phosgene are introduced with stirring over a period of one hour into a solution of 0.8 mol of 5,6-diamino-2,2-difluoro-benzodioxole, 600 ml of water and 250 ml of 37% strength by weight aqueous hydrochloric acid. Stirring is continued at 30 to 40° C. for one hour, the reaction vessel is flushed with nitrogen and the solid that is obtained is filtered off. The product is washed with water and then dried. In this manner, 160 g (92% of theory) of 6,6-difluoro-[1,3]-dioxolo-[4,5-f]-1,3-dihydro-benzimidazol-2-one are obtained in the form of a solid substance having a melting point of more than 220° C.

Example 4

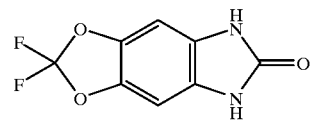
(II-1)

At room temperature, 18.8 g (0.1 mol) of 5,6-diamino-2,2-difluoro-benzodioxole are added with stirring to a mixture of 20.8 g (0.13 mol) of 1,1-carbonyl-diirnidazole and 150 ml of tetrahydrofuran, the reaction temperature rising slightly. The reaction mixture is stirred at room temperature for 18 hours and then poured into 600 ml of 1N sulphuric acid. The resulting mixture is extracted repeatedly with a total of 300 ml of diethyl ether. The combined organic phases are washed with 200 ml of water, dried over sodium sulphate and concentrated under reduced pressure. The residue that remains is stirred with 50 ml of petroleum ether. The precipitate which is obtained is filtered off with suction and dried. In this manner, 19.3 g of a product which, according to HPLC analysis, consists to 84% of 6,6-difluoro-[1,3] dioxolo-[4,5-f]-1,3-dihydro-benzimidazol-2-one are obtained. This corresponds to a yield of 76% of theory.

Melting point >220° C.

Example 5

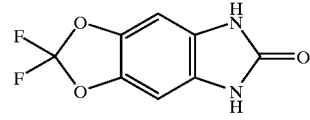
(II-1)

At 140° C., a mixture of 94 g (0.5 mol) of 5,6-diamino-2,2-difluoro-benzodioxole and 60 g (1 mol) of urea is added with stirring, a little at a time, over a period of 30 minutes to a melt of 30 g (0.5 mol) of urea. The melt is stirred at 170° C. for a further 3 hours and then cooled to 70° C. and admixed with 600 ml of 2N aqueous sodium hydroxide solution. The mixture is stirred for 30 minutes and the precipitate that is obtained is then filtered off with suction.

The filtrate is acidified with acetic acid. The resulting precipitate is filtered off with suction, washed with water and dried. In this manner, 89.5 g of 6,6-difluoro-[1,3]dioxolo-[4,5-f]-1,3-dihydro-benzimidazol-2-one are obtained. This corresponds to a yield of 83% of theory.

Example 6

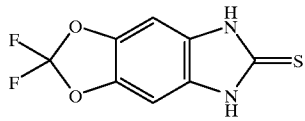
(II-2)

A mixture of 18.8 g (0.1 mol) of 5,6-diamino-2,2-difluoro-benzodioxole, 18.5 g (0.11 mol) of potassium O-ethyl-xanthate, 100 ml of ethanol and 15 ml of water is heated under reflux for 3 hours. After cooling to room temperature, nitrogen is passed through the reaction vessel and 4 g of activated carbon are added. The mixture is then heated under reflux for 15 minutes and filtered hot with suction, and the filter cake is rinsed with hot ethanol. The filtrate is heated to 60–70° C. and admixed with 100 ml of water, also of 60–70° C. A solution of 8.3 ml (0.13 mol) of glacial acetic acid in 16.7 ml of water is subsequently added. The mixture is left standing at 4° C. for 16 hours. The resulting precipitate is filtered off with suction, washed with cold water and dried over phosphorus pentoxide. In this manner, 18.1 g of a product which, according to HPLC analysis, consists to 78.34% of 6,6-difluoro-[1,3]dioxolo-[4,5-f]-1,3-dihydrobenzimidazole-2-thione are obtained. This corresponds to a yield of 62% of theory.

Example 7

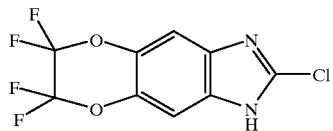
(I-2)

A mixture of 10.6 g (40 mmol) of 6,6,7,7-tetrafluoro-[1,4]dioxino-[2,3-f]-1,3-dihydro-benzimidazol-2-one and 60 ml of phosphorus oxychloride is heated under reflux for 20 hours. The reaction mixture is then poured onto 600 ml of ice. The resulting mixture is extracted twice with 150 ml of diethyl ether each time. The combined organic phases are washed with water, dried over sodium sulphate and concentrated under reduced pressure. The resulting product is chromatographed over silica gel using diethyl ether. In this manner, 4.1 g of a solid substance which, according to HPLC analysis, consists of 82% of 2-chloro-6,6,7,7-tetrafluoro-[1,4]dioxino[2,3-f]-benzimidazole are obtained. This corresponds to a yield of 30% of theory.

Example 8

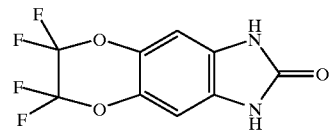
(II-3)

At room temperature, 23.8 g (0.1 mol) of 6,7-diamino-2,2,3,3-tetrafluoro-benzodioxin are added with stirring to a mixture of 16.0 g (0.1 mol) of 1,1-carbonyl-diimidazole and 150 ml of tetrahydrofuran, the temperature of the reaction mixture rising slightly. The reaction mixture is stirred at room temperature for 18 hours and then poured into 600 ml of 1N sulphuric acid. The resulting mixture is extracted repeatedly with a total of 300 ml of diethyl ether. The combined organic phases are washed with 100 ml of water, dried over sodium sulphate and concentrated under reduced pressure. The residue that remains is stirred with 30 ml of petroleum ether and 10 ml of diethyl ether. The resulting precipitate is filtered off with suction and dried. In this manner, 20.7 g of a product which, according to HPLC analysis, consists of 75% of 6,6,7,7-tetrafluoro-[1,4] dioxino-[2,3-f]-1,3-dihydro-benzimidazol-2-one are obtained. This corresponds to a yield of 59% of theory.

Example 9

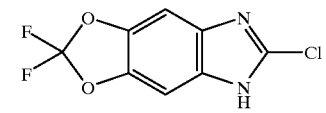
(I-1)

A mixture of 10g (44 mmol) of 6,6-difluoro-[1,3]-dioxolo-[4,5-f]-1,3-dihydro-benzimidazol-2-one and 100 ml of freshly distilled phosphorus oxychloride is heated at 120° C. in a sealed pressure vessel for 6 hours, resulting in an autogenous pressure of approximately 2 bar. The reaction mixture is subsequently concentrated under reduced pressure, admixed with ice and neutralized by addition of aqueous ammonia. The resulting residue is filtered off with suction, washed with water and dried over phosphorus pentoxide. This gives 10.35 g of a product which, according to HPLC analysis, consists of 95.6% of 2-chloro-6,6-difluoro-[1,3]-dioxolo-[4,5-f]-benzimidazole. This corresponds to a yield of 90% of theory.

Comparative Example A

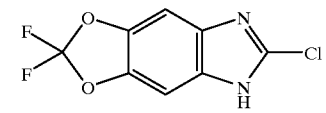
(I-1)

At 120° C., gaseous hydrogen chloride is introduced into a solution of 2.8 g (10 mmol) of 2-bromo-6,6-difluoro-[1,3]dioxolo[4,5-f]abenzimidazole in 30 ml of dimethylformamide for 2 hours. The mixture is poured into 200 g of ice/water and extracted three times with 80 ml of ethyl acetate each time. The combined organic extracts are dried over sodium sulphate and concentrated under reduced pressure. The residue is chromatographed over silica gel using diethyl ether. This gives 0.5 g (21.5% of theory) of 2-chloro-6,6-difluoro-[1,3]dioxolo[4,5-f]benzimidazole as a white solid of melting point >220° C.

Use Example I

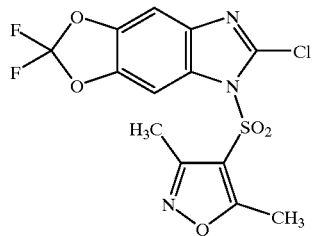

(VIII-1)

At room temperature, a mixture of 96.6 g (0.4 mol) of 2-chloro-6,6-difluoro-[1,3]dioxolo[4,5-f]benzimidazole and 600 ml of acetonitrile is admixed with stirring with 81.6 g (0.6 mol) of powdered potassium carbonate and stirred at room temperature for 10 minutes. 79.2 g (0.4 mol) of 3,5-dimethyl-isoxazole-4-sulphonyl chloride are subsequently added and the mixture is stirred at room temperature for a further 20 hours. The reaction mixture is poured into 2 litres of water. The resulting mixture is extracted three times with 500 ml of methylene chloride each time. The combined organic phases are dried over sodium sulphate and concentrated under reduced pressure. The residue that remains is chromatographed over silica gel using methylene chloride as eluent. In this manner, 117 g (75% of theory) of 1-(3,5-dimethyl-isoxazole-4-sulphonyl)-2-chloro-6,6-difluoro-[1,3]dioxolo-[4,5-f]-benzimidazole are obtained in the form of a colourless solid substance of melting point 128 to 131° C.

It will be understood that the specification and examples are illustrative, but not limitative of the present invention and that other embodiments within the spirit and scope of the invention will suggest themselves to those skilled in the art.

What is claimed is:

1. A 1,3-dihydro-benzimidazol-one of the formula

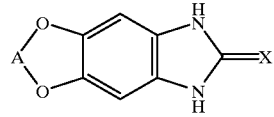

wherein

A represents the groups —$CH_2$—, —$CF_2$—, —$CCl_2$—, —$CF_2$—$CF_2$—, —CHF—$CF_2$, —CHF—CHF—, —$CF_2$—CFCl— or —CFCl—CFCl— and X represents oxygen.

2. A 1,3-dihydro-benzimidazol-one of the formula

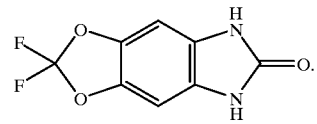

* * * * *